(12) United States Patent
Penumadu et al.

(10) Patent No.: US 6,960,756 B1
(45) Date of Patent: Nov. 1, 2005

(54) PARTICLE SIZE AND SHAPE DISTRIBUTION ANALYZER

(75) Inventors: Dayakar Penumadu, Knoxville, TN (US); Rongda Zhao, Knoxville, TN (US); Erich F. Steadman, Williamsville, NY (US)

(73) Assignee: VisionWorks LLC, Buffalo, NY (US)

( * ) Notice: Subject to any disclaimer, the term of this patent is extended or adjusted under 35 U.S.C. 154(b) by 0 days.

(21) Appl. No.: 10/294,259

(22) Filed: Nov. 14, 2002

Related U.S. Application Data (60) Provisional application No. 60/335,374, filed on Nov. 15, 2001.

(51) Int. Cl.[7] .............................. G01V 8/00; H01J 40/14
(52) U.S. Cl. .................................... 250/222.2; 356/335
(58) Field of Search ............................ 250/222.2, 573; 356/335, 336

(56) References Cited

U.S. PATENT DOCUMENTS

| | | | |
|---|---|---|---|
| 5,426,501 A * | 6/1995 | Hokanson et al. | 356/335 |
| 5,786,894 A * | 7/1998 | Shields et al. | 356/338 |
| 6,721,006 B1 * | 4/2004 | Hata | 348/294 |

FOREIGN PATENT DOCUMENTS

| | | | |
|---|---|---|---|
| EP | 0195420 A2 | * | 3/1986 |
| JP | 2000-314698 | * | 11/2000 |
| JP | 2001-165845 | * | 6/2001 |

\* cited by examiner

*Primary Examiner*—David Porta
*Assistant Examiner*—Seung C. Sohn
(74) *Attorney, Agent, or Firm*—Hodgson Russ LLP (57) ABSTRACT

A system and method for measuring the size, shape and distribution of particles wherein a digital image analysis based optical system characterizes the particle size distribution of granular and cohesion-less materials. The size and shape information is obtained in real time. Such an automated analysis system comprises the following four major components: 1) particle sizing hardware and software, 2) progressive scan CCD camera and stepper motor driven optical zoom system with large magnification ratio, 3) horizontal vibrating feeder, and 4) appropriate lighting system. In operation, the vibratory feeder allows the tested material free fall in front of the CCD camera. The backlight provided by a DC lighting system projects the free falling particles onto the camera's image plane. Pictures from free falling material are captured and transferred into the computer through a video frame grabber. The number of particles in each image is counted using specified intensity threshold and the size and shape of each particle is measured according to the calibration.

18 Claims, 8 Drawing Sheets

Fig. 1 Prototype Laboratory PSDA System

Fig. 2 Control Panel for Remotely Adjusting Magnification, Focus, and Lighting

Fig. 3 Calibration by Placing a Defining Line over Scale of Known Length

Fig. 4 Initialization Tabs

Fig. 5 Current Image Monitoring Window

Fig. 6 Report Window with Particle Size Histogram and Distribution Curve

Fig. 7 Report Window with Particle Shape Histogram and Particle Size Distribution Table Fig. 8
Flow Chart of PSDA Software Function Modules

Fig. 9

PARTICLE SIZE AND SHAPE DISTRIBUTION ANALYZER

CROSS REFERENCE TO A RELATED APPLICATION

Applicants claim priority based on U.S. provisional patent application No. 60/335,374 filed Nov. 15, 2001 and entitled "Particle Size And Shape Distribution Analyzer" which is incorporated herein by reference.

BACKGROUND OF THE INVENTION

This invention relates to the art of measuring the size, shape and distribution of particles, and more particularly to a system and method utilizing digital analysis of optical images to measure particle size, shape and distribution.

One area of use of the present invention is measuring particle size, shape and distribution of cohesion-less materials having an equivalent diameter in the wide range from about 10 µm to about 2 cm, although the principles of the present invention can be variously applied.

It would be highly desirable to provide a particle size and shape distribution analyzer which is of low cost, avoids problems associated with significant noise and vibrations often associated with sieve analysis, provides particle shape information and gives grain size distribution that is representative of the sample in a short period of time.

SUMMARY OF THE INVENTION

The present invention provides a system and method for measuring the size, shape and distribution of particles wherein a digital image analysis based optical system characterizes the particle size distribution of granular and cohesion-less materials. The size and shape information is obtained in real time. Such an automated analysis system comprises the following four major components: 1) particle sizing hardware and software, 2) progressive scan CCD camera and stepper motor driven optical zoom system with large magnification ratio, 3) horizontal vibrating feeder, and 4) appropriate lighting system. In operation, the vibratory feeder allows the tested material free fall in front of the CCD camera. The backlight provided by a DC lighting system projects the free falling particles onto the camera's image plane. Custom developed application software continuously captures the pictures from free falling material and transfers them into the computer through a video frame grabber. With appropriate magnification, focus, and lighting, high quality images of particles are obtained and displayed on the screen. Application software then counts the number of particles in each image using specified intensity threshold and measures the size and shape of each particle according to the calibration. The graphic interface is used to display the updated measurement result for current image. Using this system, around 120 frames can be analyzed in a minute. After measuring a number of images and reaching the final step of user defined convergence, the application will automatically stop acquiring the data. The software will create and display a printable report window on screen, which contains all statistical information such as particle size and shape histogram, distribution curve, and summary information on size and shape.

The following detailed description of the invention, when read in conjunction with the accompanying drawing, is in such full, clear, concise and exact terms as to enable any person skilled in the art to which it pertains, or with which it is most nearly connected, to make and use the invention.

DETAILED DESCRIPTION OF THE INVENTION

Figure 1:
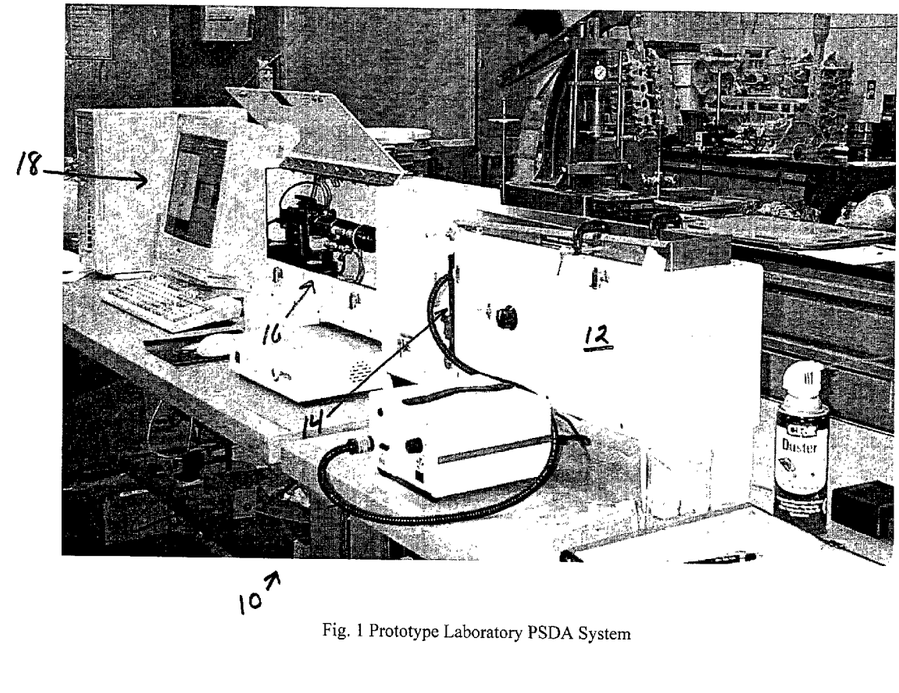
FIG. 1 is a perspective view of the apparatus of the present invention.

An illustrative form of the apparatus 10 of the present invention is shown in FIG. 1 and includes a vibratory feeder 12, a light source 14, a CCD camera 16 and a computer 18.

The optical system for a laboratory prototype utilizing the principles of the present invention consists of a CCD camera, motorized zoom lens, and lens adapters and attachments generally designated 16 in FIG. 1. The currently used CCD camera is a PULNiX TM-6702, ½" progressive scan camera with double speed scanning format (525 Lines at 60 Hz or 30 Hz). Its image sensor consists of 648(H)×484(V) effective square pixels with size of 9 µm to provide excellent image definition in all orientations. The built-in manual shutter speed control selects the electronic shutter rate from $\frac{1}{62.5}$ to $\frac{1}{16000}$ sec. in ten steps. Progressive scanning allows a full frame resolution per single shutter, resulting in crisp images of moving objects without requiring strobe lighting. Optional features include AGC enable, internal IR cut filter, and gamma adjust to 0.45. Navitar's motorized 12× Zoom System with 12 mm fine focus is used in this unit to obtain a high combination of zoom range and resolution. Both zoom and focus are gear driven by individual encoded motors and controlled by the software. With a nominal zoom range of 0.58× to 7.0×, it is designed on a modular basis offering optical quality and mechanical flexibility. The combinations with a wide range of lens adapters (from 0.67× to 2.0×) and attachments (from 0.25× to 2.0×) allow to easily choosing the magnification from 0.1× to 28.0×for measuring small particles (size range from 75 µm to 4.75 mm). Also, a Nikkon 20 mm wide-angle lens is used to reach the magnification range less than 0.1× for measuring large particles (size range from 4.75 mm to 75 mm).

Since the measurement precision depends on the brightness information of each pixel, appropriate lighting system is critical for image analysis based measurement system. Depending on the shutter speed of frame grabbing and real-time analysis, it was determined to use DC backlight with appropriate fiber optic bundles/panels for the laboratory based measurement system. The light source is generally designated 14 in FIG. 1. Currently, a FOSTEC DCR II DC regulated light source with a 150 Watts EKE lamp is used. The power supply will regulate the line voltage fluctuations of up to ±15% and the light generated will not vary more than ±0.5%. It would also eliminate flicker, dips, and surges to provide stable light output held within 1%. A built-in 9-pin connector can be accessed with an analog input to control light intensity either manually or via computer software. 2"×2" and 4"×5" backlight panels are used for small and large fields of view. Each of them can be connected to the lighting source through a 40" long fiber optic bundle to provide a very stable and uniform lighting across the frame. One advantage of using backlight is that it makes the particles appear dark against a bright background in an image to forming a clear silhouette.

The HM-100E five-axis controller with a stand along software from Spectra Services Inc. is installed in this system for remotely accessing to the motorized zoom lens and regulated lighting source. Using this controller via the PSD application software, users can conveniently push the appropriate buttons from the software interface to adjust the magnification, fine focus, and backlight until an ideal image is shown on screen. It also offers encoded control of zoom and light intensity. The correct magnification and illumination tied to a calibration for testing the specified materials can be saved in the system. Whenever the similar tests need to be performed, the predetermined magnification, illumination, and calibration can be retrieved to eliminate the user errors.

An Eriez Hi-Vi vibratory feeder generally designated 12 in FIG. 1 is used to make the being tested material free falling. It contains a 4" width tray and a 15 Watts electropermanent magnetic drive. Its feeding capacity is two tons per hour. The basic simplicity of drive powered by alternative opposing and attracting magnetic forces assures low power assumption, easy installation, and low maintenance. Since the amplitude of vibration depends directly upon the applied AC voltage, simple variation of the AC voltage from zero to maximum results in similar variation of vibratory amplitude from zero to maximum. A compact variable transformer-type controller regulates feeder speed by varying applied voltage from 0 to 100% of capacity with excellent linearity.

A 500 MHz Dell Dimension XPS T500 computer generally designated 18 in FIG. 1 is equipped with 256 MB SRAM, 17" Trinitron monitor, and a FlashBus MV Pro frame grabber. FlashBus MV Pro is a high-speed PCI-based frame grabber (bus-mastering capabilities is up to 132 Mbytes/s). It delivers consecutive frames of video in real time into system or VGA memory while the CPU is free to operate on other applications. It also has support for the capture of 60 fps non-interlaced video from progressive scan cameras, which eliminates blur seen in images of moving objects captured and transferred by standard CCD cameras. Since the FlashBus Mv Pro has low pixel jitter, it can produce extremely accurate, high-quality imaging.

Figures 8, 9:
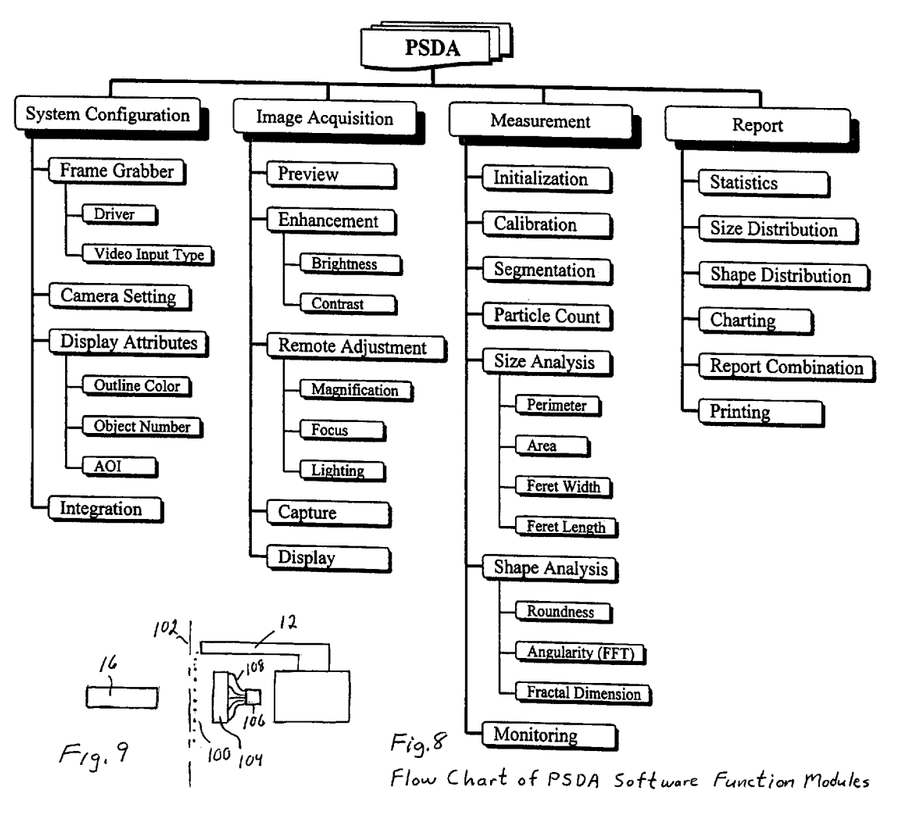
FIG. 8 is a schematic diagram illustrating function modules of the software program of the present invention.
FIG. 9 is a diagrammatic view further illustrating the apparatus of the invention.

The apparatus of the invention is illustrated further in FIG. 9 which shows particles 100 falling from vibratory feeder 12 along an image plane 102 in reference to camera 16 and the light source comprising the arrangement of panel 104 facing image plane 102, regulated DC light source 106 and fiber optic coupling 108 between light source 106 and panel 104.

The software for the particle size distribution analysis is a multiple-document interface application that was custom developed to be user friendly by using Visual Basic, Windows API, and third party software such as the scripting facility from Image-Pro Plus and optical system remote control software. The major functions include password login, remote image adjustment, calibration, measurement initialization, picture capture and display, particle counting and sizing, shape analysis, current frame analysis monitoring, process control, final result determination, measurement reporting, test result comparison, and window printing. It also contains a standard text editor for editing the initialization, measurement, and report documents. All functions can be directly accessed from the main menu, toolbar, or popup menus in application main window. The particle size distribution test is controlled to continuously capture an image, display it on the image window, threshold the particles, measure the size and shape of each particle, record the analysis result, and display the analysis result on the current monitoring window. After system captures each 100 frames, the program will analyze the particle size distribution using the information of captured images so far and compare it with last particle size distribution result. If the standard deviation of these two results is less than the specification, the program will automatically stop the test, create and save the final report, and display the report on a report window. The foregoing is illustrated by the screen displays of FIGS. 2–7 and the diagram of software function modules set forth in FIG. 8.

Particle sizing is implemented in the following manner. With a wide range of lens adapters and attachments available, it allows in easily choosing the magnification, field of view, and working distance for a given material whose size and/or shape information is of interest. However, the magnification is always in conflict with the field of view. Using a larger magnification can usually yield a more accurate measurement for each captured particle, but smaller field of view and less number of particles contained in an image. The compromise between the magnification and field of view that is used assumes that the smallest particle in the tested material should be presented by at least 5 pixels in diameter and largest particle should be presented by at most 100 pixels in diameter in an image. By following this rule, the particle size range is limited to be 20 (i.e. largest particle size <=20×smallest particle size). For example, 0.6× optical magnification could be used to test the material with particle size between 75 $\mu$m and 1.5 mm.

Figure 2:
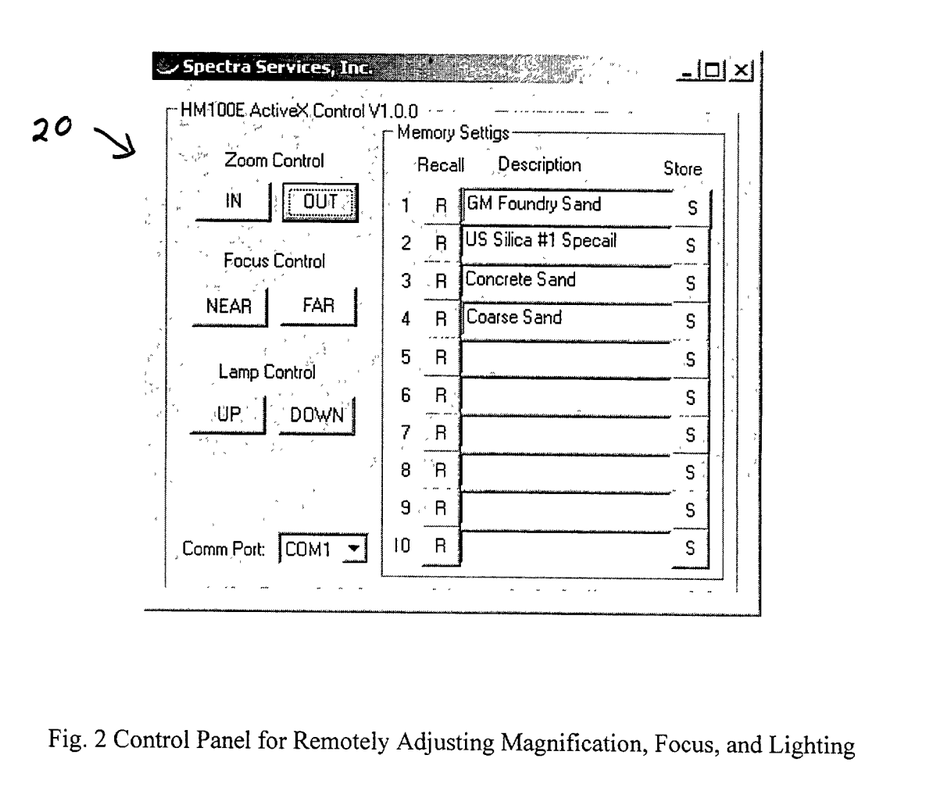
FIG. 2 is a screen display illustrating a control panel for remotely adjusting magnification, focus and lighting.

Since the camera captures the images while the particles are free falling, the $\frac{1}{4000}$ sec. to $\frac{1}{10000}$ sec. shutter speeds are used to keep away from blurring the outline of particles. In addition, to capture high quality images of tested material adjustments are provided for magnification, focus, and intensity settings via custom software. Analyzer program provides an optical control panel window 20 as shown in FIG. 2. Pushing these buttons in this window can conveniently operate a controller for remotely adjusting the magnification, focus, and intensity till the particles in a given image can be accurately identified and analyzed. The magnification for the material of known size range should be adjusted to meet the above assumption i.e. the particles presented in an image should occupy 5 to 100 pixels. Using motorized fine focus, the working distance could be changed in ±7 mm to very smoothly adjust the focus. The DC lighting panel is placed just behind the object plane to provide a stable and uniform backlight. To create a bright background against the dark particle projections, the intensity value of each pixel appearing on background should be adjusted over 240. Once a satisfactory optical setting has been obtained the current encoded magnification, focus, and intensity settings can be assigned to a memory setting button on the control panel window. Whenever one clicks on its recall button, the current adjustment will be retrieved for testing the similar materials.

Figure 3:
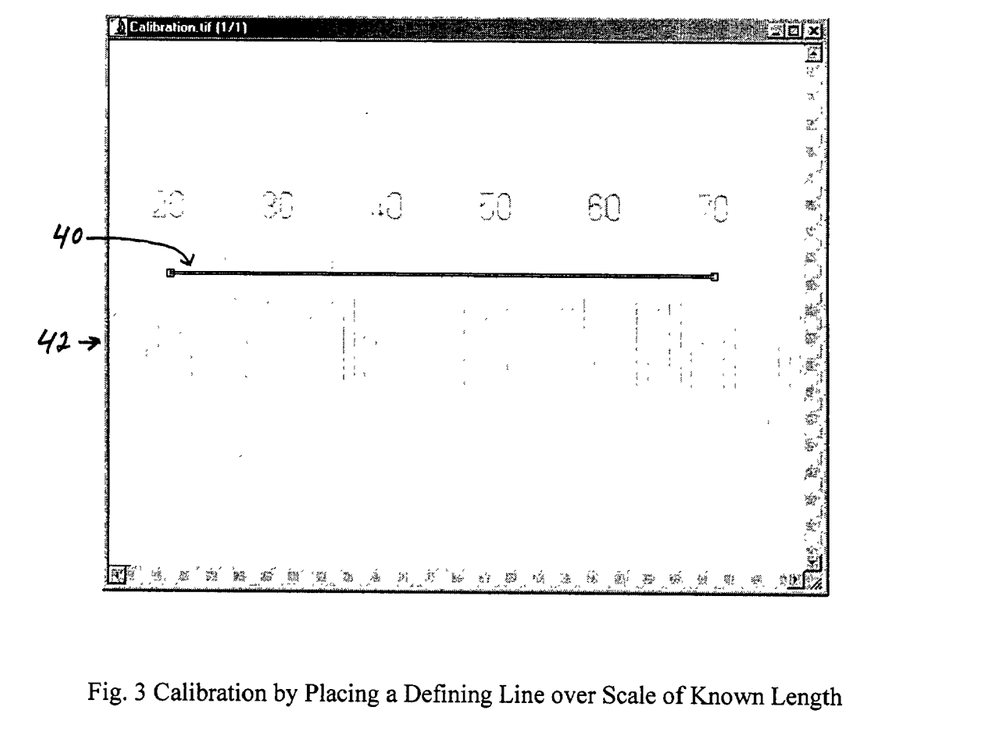
FIG. 3 is a screen display illustrating calibration by placing a defining line over a scale of linear length.

Under a selected magnification, the calibration must be done before a test. To do so, one can place a calibration scale at the object plane and snap an image that shows the scale. Then an adjustable defining line can be positioned horizontally over the scale of known length as shown in FIG. 3. By giving the real length of defining line, the calibration function counts the number of pixels that the defining line contains and determines the actual image scale i.e. the number of pixels per unit. This calibration must be saved into a calibration file. The measurement will use it to convert the number of pixels that a particle contains in an image to its real size.

Figure 4:
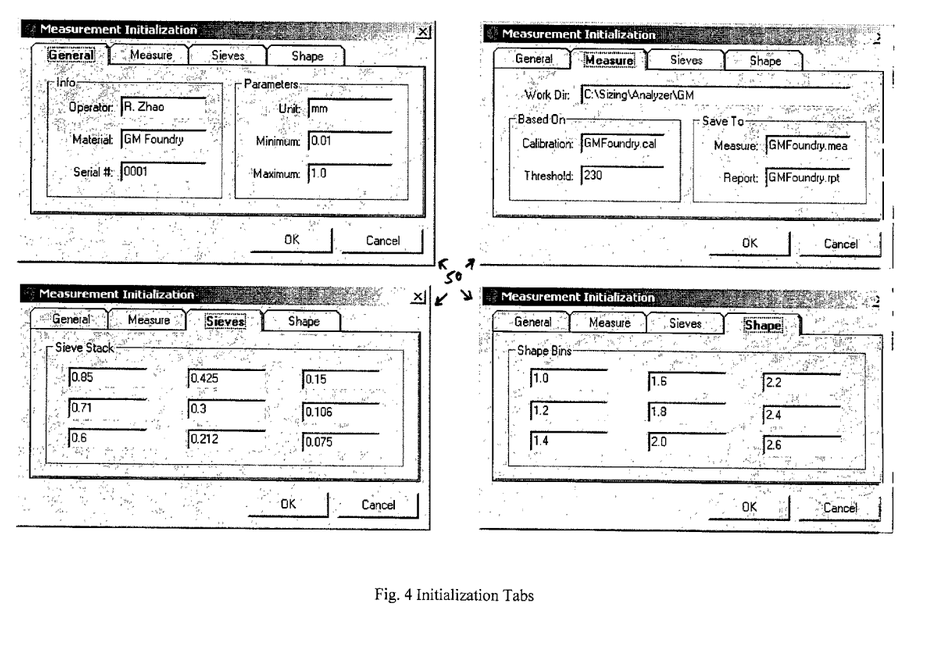
FIG. 4 is a series of screen display illustrating initialization tabs.

Analyzer provides a dialog box to initialize a test as shown in FIG. 4. This dialog box consists of four tabs: General Information, Measurement Setting, Sieve Stack, and Shape Classification. To perform a test, the system needs an initialization process. In the General Information tab, system will ask the operator's name, materials' name, serial number of product, calibration unit, and the interested range of particle size. In the Measurement Setting tab, the intensity threshold for identifying the particles, working directory path, calibration file name, and the file names to save the measurement result and final report must be provided. The Sieve Stack tab allows users to select nine sieves beginning from largest mesh opening to simulate a sieve analysis. The sieve stack can be very flexibly combined by using any size, but it is suggested to select the mesh opening from the standard sieve sizes. Since the system has the functions to determine the roundness of each particle, it needs the roundness classification bins to do the particle shape analysis. In this system, the roundness of a perfect sphere is defined to be one. The larger roundness value means more deformed from the sphere. Depending on the material being tested, there are nine roundness bins that can be defined beginning from one in the Shape Classification tab. The above initialization can be used for the current test and can also be saved into an initialization file for another tests to reference.

The vibratory feeder is used to make a free falling particle flow at the object plane. The material being tested is poured to the end of 20" long vibratory tray. At its front end, the material free falls vertically into the object plane. The feeder speed can be simply controlled by changing the AC input voltage from 0 to 110 v to control the number of particles that can be captured in an image. To avoid the particle touching problem, the number of particles captured in any image should be less than 30.

Based on the calibration and initialization, the on-line test can automatically run until the completion of analyzing the size and shape information of a given material. In summary, selecting Start command from Toolbar in the application main window will start a new test. The program captures a single image from free falling particles through frame grabber, transfers it into the system memory and displays the image on an image window. Using the intensity threshold defined in the initialization process, the program identifies all particles in this image. The particles that touch the designated edges of the image field are excluded automatically. According to the calibration, the program measures the smallest caliper length, perimeter, and area of each particle, but only the particles meeting the interested range defined during the initialization will be counted. Simultaneously, the counted particles will be colored and the image window will be updated for observation. The obtain results in sieve analysis format, the smallest caliper length of a particle is used to determine its size and the area information is used to evaluate its weight.

Figure 5:
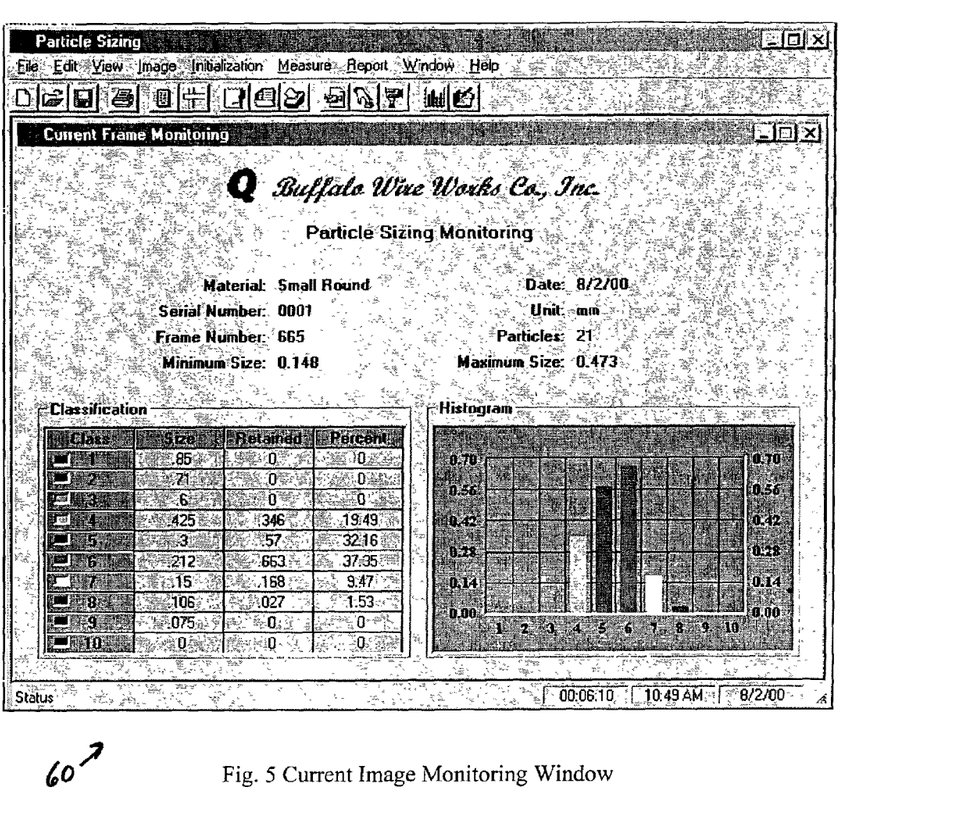
FIG. 5 is a screen display illustrating an image monitoring window.

Accordingly, the statistical data of counted particles are calculated such as their minimum and maximum sizes. The counted particles are classified into 10 bins using predefined sieve stack. The amount of the particles in each bin is then calculated. After the completion of particle sizing analysis for the current image, the result will be displayed in a data table and a histogram on the monitoring window as shown in FIG. 5. The measurement and analysis data are also saved in a measurement data file for creating the final report later. During a test, system repeatedly performs above processes. The program will analyze the particle size distribution once after system captures 100 images each time. This analysis is similar to the individual frame analysis described above, but based on the measurement data of counted particles in all 100 captured images. The analysis function first classifies all particles into 10 bins according to predefined sieve stack and computes the amount of particles in each bin. Then it compares the amount of particles in each bin with last analysis result. If the standard deviation of these two analysis results is greater than the criterion, the program will save the analysis result, continue to measure another 100 images. Then it reanalyzes a new particle size distribution and compares the result with last one until the standard deviation of two successive analysis results is less than the criterion. Upon convergence, the program will automatically stop the test and save the measurement data into a disk file.

Figure 6:
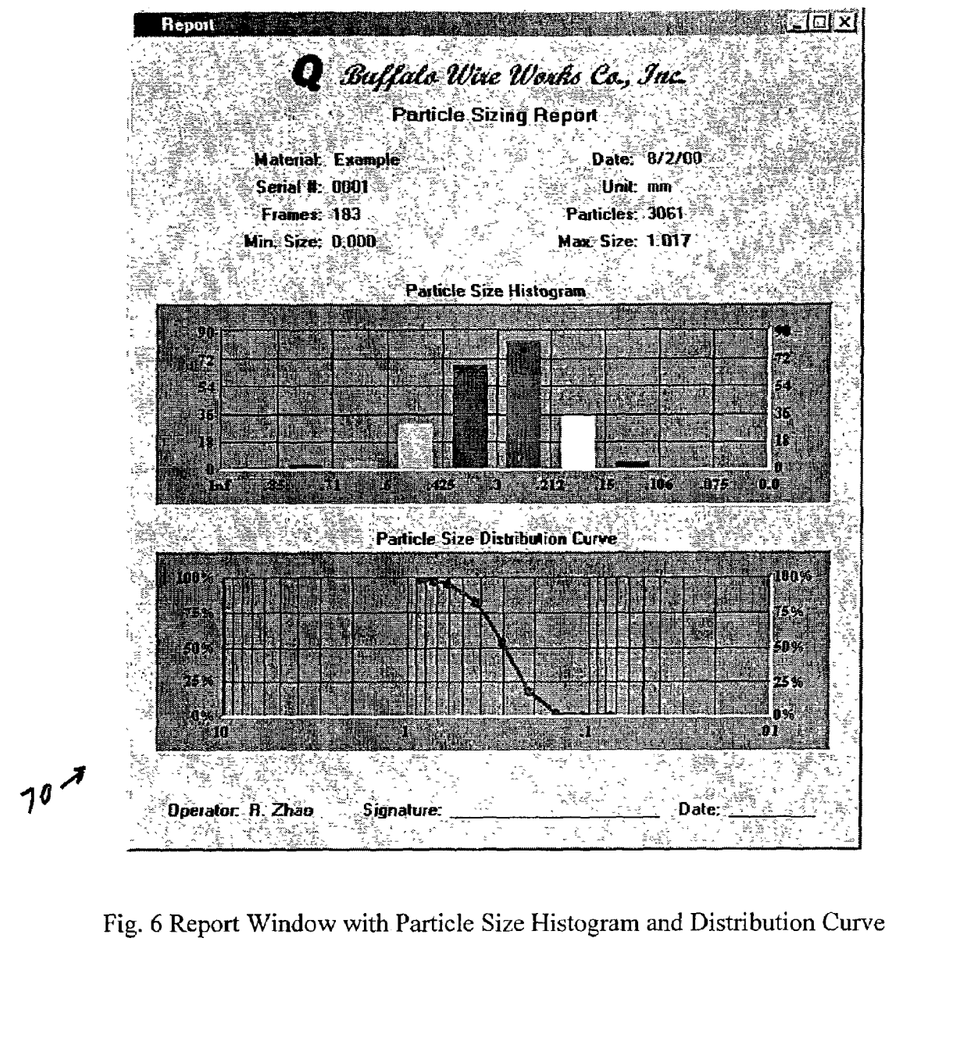
FIG. 6 is a screen display illustrating a report window with particle size histogram and distribution curve.
Figure 7:
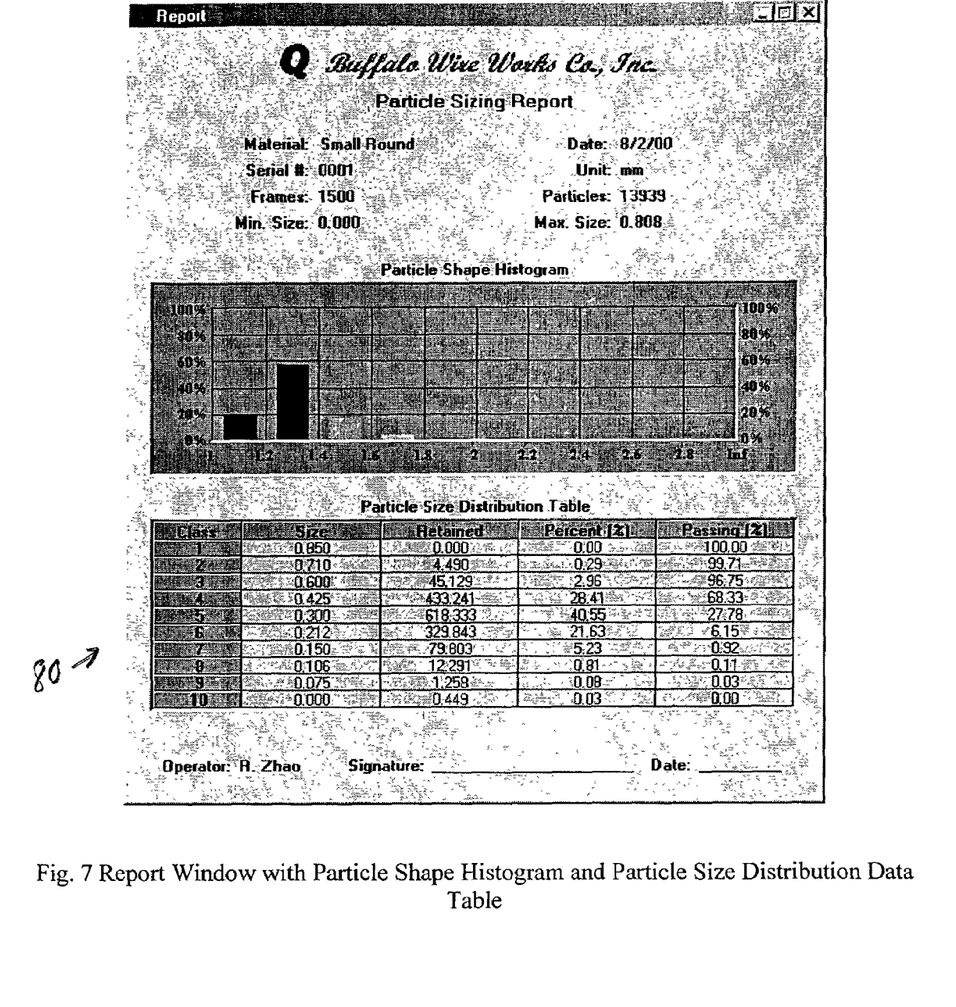
FIG. 7 is a screen display illustrating a report window with particle shape histogram and particle size distribution data table.

Once a test has reached the final result, the program will immediately create a report for this test. The program also computes the percent retained in each bin by dividing the amount of particles in each bin by the total amount by volume. Then the percent passing (or percent finer) is computed. The built-in particle shape analysis function is superior to the traditional sieve analysis. It analyzes the roundness of every counted particle. The roundness of counted particles is also classified into 10 bins on the basis of shape classification definition mentioned before. The analysis results are displayed on a popup report window as shown in FIG. 6. The general information of a test is displayed on the top of report window such as the material name, measurement unit, number of captured images, total number of counted particles and their minimum and maximum sizes. The particle size classification result is displayed in a histogram by the particle size bins versus the amount of particles. A logarithmic plot of particle size versus percent passing is drawn next to the histogram to shown the particle size distribution of tested material. The detail analysis data and shape analysis result can also be provided on the report window by double click the title of particle size distribution plot and particle size histogram, respectively. They are shown in FIG. 7. The analysis data table contains the analysis data related to the amount retained, percent retained, and percent passing in each classification bin (or each sieve). In the shape classification histogram, the roundness classification result is drawn by the classification bins versus the number of particles. The analysis data, including general information, particle size histogram, particle size distribution, and particle roundness, are also saved into a file. In addition, the program provides a standard text editor to prepare an initialization file, read the measurement data, and open and print a report. Using powerful window printing functions, the image, monitoring, and report windows can be easily printed to obtain hard copies of the results.

In conclusion, an automatic particle size, shape, and its distribution analysis (PSDA) testing system is provided that uses a novel concept of digital image analysis using hardware and software to measure the particle size, shape, and its distribution for various materials. The technology described in the illustration presented herein is specifically applied to measure particle size distribution of cohesion-less materials having an equivalent diameter that falls in the range of 25 $\mu$m to 40 mm. PSDA has the following four major components: 1) particle sizing hardware and software, 2) stepper motor driven high magnification optical lens system, 3) horizontal vibrating feeder, and 4) appropriate lighting system. For the laboratory prototype unit, the following specific components were used. A high-speed personal computer with sufficient RAM (256 MB) and video memory, and video frame grabber constitute the computer hardware. Visual Basic is used to write the application software with dynamic links to the Image-Pro library for frame grabbing, converting gray images to binary images with proper threshold techniques, and appropriate filtering. A progressive scan CCD camera with large range magnification adjustment options are used to obtain high contrast gray images of the free falling particles. PSDA is anticipated to have significant applications in areas such as highway materials, foundry casting, processed food, pharmaceutical, copying (inks and toner), and ceramic industries. In addition to determining size and its distribution, PSDA can also evaluate particle shape using various descriptors including aspect ratio and roundness.

Thus, the system and method of the present invention provides particle size distribution rapidly and also gives information on shape of the particles. The results obtained using the present invention indicate good agreement with other procedures such as traditional vibratory sieve analysis method and laser light scattering techniques. The advantages of the system and method of the present invention are its low cost, avoidance of problems associated with significant noise and vibration often associated with sieve analysis, providing particle shape information and providing grain size distribution that is representative of the sample in a short period of time.

What is claimed is:

1. A system for providing information on size and/or shape of particles comprising:
   a) a progressive scan CCD camera having an image plane;
   b) a vibratory feeder for receiving material consisting of particles to be investigated and for causing the particles in the quantity of material to free fall along the image plane in a controlled manner;
   c) a light source for illuminating the particles as they fall through the image plane and disposed to direct light in a direction for back-lighting the particles relative to the camera;
   d) a computer operatively coupled to said camera for displaying images of the particles and information obtained on the size and/or shape of the particles, the computer having a memory and being provided with a frame grabber to deliver consecutive frames of video in real time to the computer memory under control by the computer, the computer containing stored program means for counting the number of particles in each image using a specified intensity threshold and for measuring the size and/or shape of each particle according to a calibration, the computer being operatively coupled to the light source and containing stored program means for controlling operation of the light source and the computer containing stored programs means for controlling zoom and focus of the CCD camera.

2. The system according to claim 1, wherein the light source comprises a panel facing the image plane, a regulated DC light source and a fiber optic coupling between the DC light source and the panel.

3. The system according to claim 1, wherein the stored program means includes a component to continuously capture images, a component to display images, a component to threshold particles, a component to measure the size and/or shape of each particle, a component to record the result of the measure and a component to display the result of the measure.

4. The system according to claim 3, wherein the stored program means includes a component to analyze particle size and/or shape distribution using information of captured images from a predetermined number of frames and a component to compare the result with a previously obtained distribution.

5. The system according to claim 3, wherein the stored program means includes a component to obtain particle size information according to a sieve analysis format.

6. The system according to claim 3, wherein the stored program means includes a component to obtain particle shape information according to a sieve analysis format.

7. A method for providing information on size of particles comprising:
   a) providing a quantity of material consisting of particles to be investigated;
   b) providing a progressive scan CCD camera having an image plane;
   c) causing the particles in the quantity of material to free fall along the image plane in a controlled manner;
   d) illuminating the particles as they fall through the image plane;
   e) utilizing the CCD camera to capture successive images of the particles falling through the image plane;
   f) controlling the illumination of the particles and the zoom and focus of the camera by means of a computer;
   g) processing the images in the computer; and
   h) utilizing a predetermined number of processed images to provide particle size information.

8. The method according to claim 7, wherein the particles are caused to free fall using a vibratory feeder.

9. The method according to claim 7, wherein the CCD camera is disposed facing one side of the image plane and wherein the particles are illuminated by a light source disposed to direct light toward the opposite side of the image plane so that the particles are back-lighted as they fall through the image plane.

10. The method according to claim 7, wherein processing the images includes delivering consecutive frames of video in real time into the computer memory.

11. The method according to claim 10, wherein processing the images further comprises continuously capturing images, applying a threshold to the particles in an image, measuring properties of each particle including size and/or shape and recording the results of measuring.

12. The method according to claim 11, wherein measuring properties of each particle comprises:
   a) establishing a particle size range according to selected numbers of pixels in particle diameters;
   b) establishing a calibration function for counting the number of pixels that the calibration defines to provide a factor in the form of number of pixels per unit; and
   c) converting the number of pixels that a particle contains in an image to real particle size.

13. The method according to claim 12, further including obtaining particle size information according to a sieve analysis format.

14. The method according to claim 12, further including obtaining particle shape information according to a sieve analysis format.

15. The method according to claim 10, further comprising displaying the captured images.

16. The method according to claim 10, further comprising displaying the results of the measuring.

17. The method according to claim 10, further including analyzing an obtained particle size and/or shape distribution utilizing results of measuring from a predetermined number of captured frames.

18. The method according to claim 17, further including comparing the particle size and/or shape distribution to a previously obtained particle size and/or shape distribution and determining the standard deviation there between.

* * * * *